United States Patent [19]
Lemann et al.

[11] Patent Number: 6,042,842
[45] Date of Patent: Mar. 28, 2000

[54] COSMETIC COMPOSITION COMPRISING A NOVEL PIGMENT

[75] Inventors: Patricia Lemann, Creteil; Jean-Christophe Simon, Paris, both of France

[73] Assignee: L'Oreal S.A., Paris, France

[21] Appl. No.: 09/276,812

[22] Filed: Mar. 26, 1999

[30] Foreign Application Priority Data

Mar. 27, 1998 [FR] France ................................. 98 03839

[51] Int. Cl.[7] .......................... A61K 7/00; A61K 7/021; A61K 7/025; A61K 31/40
[52] U.S. Cl. ............................ 424/401; 424/63; 424/64; 424/400; 514/412; 514/421
[58] Field of Search .................... 424/63, 64, 400, 424/401; 514/412, 421

[56] References Cited

FOREIGN PATENT DOCUMENTS

| | | |
|---|---|---|
| 0 542 669 | 5/1993 | European Pat. Off. |
| 0 787 730 | 8/1997 | European Pat. Off. |
| 0 787 731 | 8/1997 | European Pat. Off. |
| WO 96/08537 | 3/1996 | WIPO |
| WO 98/56859 | 12/1998 | WIPO |

OTHER PUBLICATIONS

J.–B. Galey et al., "Ethylene formation from methionine as a method to evaluate oxygen free radical scavenging and metal inactivation by cosmetics", International Journal of Cosmetic Science, vol. 13, No. 2, Apr. 1991, pp. 65–78.
English language Derwent Abstract of EP 0 787 730.
English language Derwent Abstract of EP 0 787 731.

*Primary Examiner*—Shelley A. Dodson
*Attorney, Agent, or Firm*—Finnegan, Henderson, Farabow, Garrett & Dunner, L.L.P.

[57] ABSTRACT

The present invention relates to cosmetic compositions, in particular make-up cosmetic compositions, comprising a novel red pigment with an intense and saturated color which does not generate free radicals. This novel pigment is a diketopyrrolopyrrole (DPP) of formula:

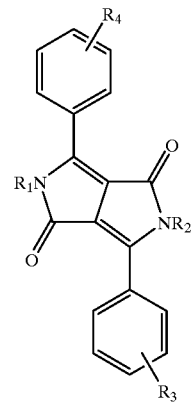

in which $R_1$ and $R_2$ independently represent a hydrogen atom, a $C_1$ to $C_{18}$ alkyl radical, a $C_3$ to $C_{12}$ alkenyl radical, a $C_2$ to $C_5$ alkoxycarbonyl radical or a phenyl radical which is optionally substituted by a halogen and $R_3$ and $R_4$ independently represent a hydrogen atom, a $C_1$ to $C_{18}$ alkyl radical, a $C_1$ to $C_4$ alkoxy radical, a halo radical or a phenyl radical, or a —$SO_3M$ group with M being a hydrogen atom, a metal atom or an ammonium group, it being possible for the alkyl, alkenyl and alkoxy radicals to be linear or branched. By virtue of this pigment, it is possible to protect the skin, lips and keratinous fibers from free radicals without using antioxidizing agents in the composition.

39 Claims, No Drawings

COSMETIC COMPOSITION COMPRISING A NOVEL PIGMENT

The present invention relates to cosmetic compositions comprising a novel red pigment with an intense and saturated colour which does not generate free radicals and, more especially, to compositions for making up the skin, both of the face and of the human body, keratinous fibres or superficial body growths, such as the nails, eyelashes, eyebrows or hair, and the lips.

Makeup compositions, such as free or compacted powders, foundations, face powders, eyeshadows, lipsticks, products for concealing rings under the eyes, blushers, mascaras, eyeliners, lip pencils, eyeliner pencils, nail varnishes and products for making up the body are composed of an appropriate vehicle and of colouring agents of different natures intended to confer a certain colour on these compositions before and/or after their application to the skin, lips and/or superficial body growths.

These colouring agents can be lakes, inorganic or organic pigments and/or pearlescent pigments or alternatively colorants. In the red pigments range, cosmetic scientists have available pigments of inorganic origin, such as red iron oxides or mixtures of brown-yellow iron oxides, and pigments of organic origin. Inorganic pigments, in particular inorganic oxides, have the advantage of being very stable but have the disadvantage of giving rather drab and pale colours. Organic lakes have the advantage of conferring vivid colours on the compositions but the majority are unstable with respect to light, temperature or pH. Some of these lakes also exhibit the disadvantage of staining the skin in an unsightly way after application, by escape of the colorant. Pearlescent pigments, for their part, make it possible to obtain varied but never intense colours with effects which are iridescent but which are generally fairly weak.

Furthermore, some colouring agents exhibit the disadvantage of generating free radicals in the make-up formulae, modifying the rendering of the colours and the stability of the compositions, and then on the skin after application, which promotes cutaneous ageing (appearance of wrinkles, fine lines or yellowing of the skin). Colouring agents exhibiting this disadvantage are mixtures of brown-yellow iron oxides sold under the trade name "Sicomet Brun ZP 3569" by BASF, for example, pigments of organic origin, such as Flaming Red (D&C Red No. 36, Colour Index 12085), sold under the trade name D&C Red 36W 008 by Wacker, and the aluminium lake of phloxine B on alumina (D&C Red No. 27 Aluminium Lake).

Today, antioxidizing agents, such as, for example, ethoxyquin, are used in order to overcome this disadvantage. Unfortunately, it is often difficult, due to the multiplicity of ingredients present in make-up compositions, to find an antioxidizing agent which is 100% effective. Furthermore, antioxidizing agents themselves often generate degradation products (oxidation of the antioxidizing agent), which products can be a nuisance.

One aspect of the invention is specifically the use, in a cosmetic composition, of a novel red pigment with an intense and saturated colour which is stable and which has the advantage of generating far fewer free radicals than the pigments conventionally used, in particular in order to obtain a red colour.

The inventors have surprisingly found that diketopyrrolopyrroles (abbreviated to DPP) make it possible to limit the production of free radicals, since they have the property of generating very few free radicals, and thus to avoid the use of antioxidants in the compositions. In addition, these pigments make it possible to obtain an intense coloration and in particular a very vivid and intense vermillion which does not escape over the skin and which is stable with respect to light, pH and temperature.

Specifically, one aspect of the invention is a coloured composition for topical application and more specifically a cosmetic make-up composition comprising a pigment of formula (A):

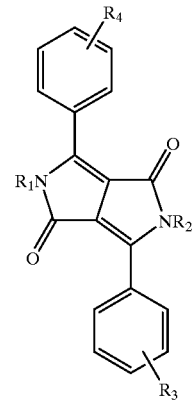

in which $R_1$ and $R_2$ independently represent a hydrogen atom, a $C_1$ to $C_{18}$ alkyl radical, a $C_3$ to $C_{12}$ alkenyl radical, a $C_2$ to $C_5$ alkoxycarbonyl radical or a phenyl radical optionally substituted by a halogen and $R_3$ and $R_4$ independently represent a hydrogen atom, a $C_1$ to $C_{18}$ alkyl radical, a $C_1$ to $C_4$ alkoxy radical, a halo radical, a phenyl radical, or a $SO_3M$ group with M representing a hydrogen atom, a metal atom or an ammonium group, it being possible for the alkyl, alkenyl and alkoxy radicals to be linear or branched. The $R_3$ radicals can be at the 2, 3, 4, 5 or 6 position and preferably at the 4 position. The metal M can be sodium, potassium, or lithium.

The alkyl and alkoxy radicals can be linear or branched and can be chosen for example, from methyl, ethyl, n- and isopropyl, n-, sec-, tert- or isobutyl, n-, sec-, tert- or isopentyl radicals; the alkenyl radicals can be linear or branched and can be chosen for example from allyl, methallyl, 2-butenyl, 2-hexenyl, 3-hexenyl or 2-octenyl radicals. The halogen atom can preferably be Cl or F. Preferably, $R_1$ and $R_2$ independently represent a hydrogen atom or a methyl or 4-chlorophenyl radical. Advantageously, $R_3$ and $R_4$ are independently chosen from a hydrogen atom and 4-chloro and 4-tert-butyl radicals.

The pigment of the invention may be transparent or opaque and may optionally be combined with other pigments for increasing the stability of said pigment and of the composition of the invention when exposed to light and the elements as mentioned in the document WO-A-98/56859, the disclosure of which is specifically incorporated by reference herein, or for enhancing the color power and/or goniochromatic properties of crystal liquid or multilayer pigments having goniochromatic properties.

The manufacture of the diketodiarylpyrrolo-pyrroles of formula (A) is disclosed in particular in the Ciba-Geigy documents EP-A-542,669, EP-A-787,730, EP-A-787,731 and WO-A-96/08537.

A preferred compound is "Rouge Irgazine DPP-Red BO", listed in the Colour Index (abbreviated to CI) as Pigment Red 254-No. CI 56110. It is pyrrolo[3,4-c]pyrrole-1,4-dione, the two benzene rings of which are dihydrogenated at the 2 and 5 positions and chlorinated at the 4 position. This compound exhibits the following formula (B):

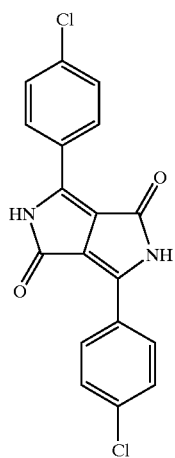

Additional preferred "DPP" pigments which can be used in the composition of the invention, are, for example:

Cromophtal DPP Red BP P—CI Pigment Red 254-No. CI 56110;

Cromophtal DPP Red BP—CI Pigment Red 254-No. CI 56110;

Irgazine DPP Red 5G—CI Pigment Red 255;

Irgazine DPP Rubine TR—CI Pigment Red 264;

Irgazine DPP Red 5049 B—CI Pigment Red 270;

Irgazine Orange RA—CI Pigment Orange 73.

To demonstrate the property which DPP has of not generating free radicals, the inventors have carried out an ethylene test according to the process described in the article "Ethylene formation from methionine as a method to evaluate oxygen free radical scavenging and metal inactivation by cosmetics" by J.-B. Galey, F. Millecamps and Q.-L. Nguyen, International Journal of Cosmetic Science, 13, 65–78, 1991, the disclosure of which is specifically incorporated by reference herein.

The object is to compare the behaviour of the organic pigment according to the invention with respect to that of conventional pigments in a photooxidation test using iron as a generator of free radicals.

In the measurement procedure of the ethylene test, the $FeCl_3$ used to activate the production of free radicals has been substituted by each of the pigments to be tested. The results are given in the table below:

| ETHYLENE PRODUCED (peak surface area) | | | |
|---|---|---|---|
| COLORANTS | | | |
| concentration | 0.0001% | 0.002% | 0.02% |
| Brown, yellow iron oxide | 6641 | 14,213 | 9708.5 |
| Flaming Red | 4447 | 3316.5 | 2579.5 |
| DPP | 1854 | 2215 | 1903 | the 0.005% $FeCl_3$ control being on average at 9000 (arbitrary unit, relative measurement). The greater the amount of ethylene, the greater the production of free radicals.

The starting materials brown, yellow iron oxide (CI 77491+CI 77492) and Flaming Red (CI 12085) are not inert. At low doses, they activate the production of free radicals until a concentration is reached where the protective effect of the pigment begins to come into play, whereas, for DPP, the level of ethylene produced is very low with respect to the two others and does not change as a function of the concentration. This pigment may therefore be advantageously used in make-up compositions and coloured anti-sun compositions, in particular coloured compositions intended for the protection of the skin and/or mucous membranes, such as the lips, without generating free radicals, and can therefore limit damage to the skin and/or mucous membranes.

The pigment according to the invention may be incorporated in a cosmetic composition, in particular a make-up composition, in an amount which can be easily determined by a person skilled in the art on the basis of his broad knowledge and which can in particular range from 0.01 to 50% by weight with respect to the weight of the composition, preferably in an amount ranging from 0.5 to 25% by weight. This pigment can be also fixed on a polymer in particular by graphing or embedding.

The composition of the invention can be provided in the form of a product to be applied to the lips, eyes, skin and/or superficial body growths. It thus comprises a cosmetically acceptable medium, that is to say a medium compatible with all keratinous substances, such as the skin, both of the human body and of the face, nails, hair, eyelashes and eyebrows. This medium can comprise or be provided in particular in the form of a suspension, dispersion or solution in solvent or aqueous or aqueous/alcoholic medium, optionally thickened or even gelled; an oil-in-water, water-in-oil or multiple emulsion; a gel or foam; an emulsified gel; a dispersion of vesicles, in particular of ionic or non-ionic lipids; a two-phase or multiple-phase lotion; a spray; a loose, compacted or cast powder; or an anhydrous paste. A person skilled in the art can choose the appropriate dosage form, such as pharmaceutical dosage form, as well as its method of preparation, on the basis of his broad knowledge, taking into account, on the one hand, the nature of the constituents used, in particular their solubility in the vehicle, and, on the other hand, the application envisaged for the composition.

When the composition according to the invention is provided in the form of an emulsion, it may in addition comprise a surfactant, preferably in an amount ranging from 0.01 to 30% by weight with respect to the total weight of the composition.

Depending on the application envisaged, the composition may additionally comprise a film-forming polymer (such as nitrocellulose, hydrocarbons-comprising resin and/or silicone resin). This is in particular the case when it is desired to prepare a composition, such as a nail varnish, mascara or eyeliner, or a hair composition, such as a lacquer. The polymers can be dissolved or dispersed in the cosmetically acceptable medium and can optionally be combined with coalescence agents and/or plasticizers.

The composition according to the invention may also comprise a fatty phase, composed in particular of fatty substances which are liquid at room temperature (generally 25° C.) and/or of fatty substances which are solid at room temperature, such as waxes, pasty fatty substances, gums and mixtures thereof.

Preferred fatty substances which are liquid at room temperature, often known as oils, which can be used in the invention, are, for example: hydrocarbon-comprising oils of animal origin, such as perhydrosqualene; vegetable hydrocarbon-comprising oils, such as liquid triglycerides of fatty acids comprising 4 to 10 carbon atoms, such as triglycerides of heptanoic or octanoic acids, or sunflower, maize, soybean, grapeseed, sesame, apricot, macadamia, castor or avocado oils, triglycerides of caprylic/capric acids, jojoba oil or karite butter; linear or branched hydrocarbons of mineral or synthetic origin, such as liquid paraffins and derivatives thereof, petroleum jelly, polydecenes or hydrogenated polyisobutene, such as parleam; synthetic esters and ethers, in particular of fatty acids, such as, for example, purcellin oil, isopropyl myristate, 2-ethylhexyl palmitate, 2-octyldodecyl stearate, 2-octyidodecyl erucate or isostearyl isostearate; hydroxylated esters, such as isostearyl lactate, octyl hydroxystearate, octyidodecyl hydroxystearate, diisostearyl maleate, triisocetyl citrate or heptanoates, octanoates or decanoates of fatty alcohols; polyol esters, such as propylene glycol dioctanoate, neopentyl glycol diheptanoate, diethylene glycol diisononanoate and pentaerythritol esters; fatty alcohols having from 12 to 26 carbon atoms, such as octyldodecanol, 2-butyloctanol, 2-hexyldecanol, 2-undecylpentadecanol or oleyl alcohol; partially hydrocarbon-comprising and/or silicone-comprising fluorinated oils; silicone oils, such as linear or cyclic, volatile or non volatile polydimethylsiloxanes (PDMS) which are liquid or pasty at room temperature, such as cyclomethicones, dimethicones, optionally comprising a phenyl group, such as phenyl trimethicones, phenyltrimethylsiloxydiphenylsiloxanes, diphenylmethyldimethyltrisiloxanes, diphenyl dimethicones, phenyl dimethicones or polymethylphenylsiloxanes; or mixtures thereof.

These oils can represent from 0 to 100% by weight with respect to the total weight of the fatty phase.

The composition according to the invention can furthermore comprise any ingredient conventionally used in the fields concerned and more especially in the cosmetics and dermatological fields. These ingredients are in particular chosen from preservatives, aqueous-phase thickeners (polysaccharide biopolymers or synthetic polymers) or fatty-phase thickeners, fragrances, hydrophilic or lipophilic active principles and mixtures thereof. The amounts of these various ingredients are those conventionally used in the fields concerned and are, for example, from 0.01% to 20% of the total weight of the composition. The nature of these ingredients and their proportion in the production of compositions according to the invention can result in compositions which are stable, thickened and glossy. The composition can also comprise water at a concentration ranging from 0 to 98% of the total weight of the composition.

Moreover, the composition of the invention may comprise an additional particulate phase which may be present in an amount ranging from 0 to 35% of the total weight of the composition, preferably from 0.05 to 20%, and which may further comprise pigments, and/or pearlescent agents, and/or fillers used in cosmetic compositions.

Pigments should be understood as comprising inorganic or organic, white or coloured particles which are insoluble in the liquid fatty phase and which are intended to colour and/or opacify the composition. Fillers should be understood as comprising lamellar or non-lamellar, inorganic or synthetic, colourless or white particles. Pearlescent agents should be understood as comprising iridescent particles, in particular produced by certain molluscs in their shell, or else synthesized. These fillers and pearlescent agents are used in particular to modify the texture of the composition.

Pigments other than DPP may be present in the composition in an amount ranging from 0 to 25% of the weight of the final composition and preferably from 2 to 15%. Preferred inorganic pigments are, for example, titanium, zirconium or cerium oxides, as well as zinc, iron or chromium oxides and ferric blue. Preferred organic pigments are, for example, carbon black and barium, strontium, calcium and aluminium lakes.

The pearlescent agents may be present in the composition in an amount ranging from 0 to 20% of the total weight of the composition, preferably from 1 to 15%. Preferred pearlescent agents are, for example, mica covered with titanium oxide, with iron oxide, with natural pigment or with bismuth oxychloride, such as coloured titanium oxide-coated mica.

The fillers may be present in an amount ranging from 0 to 35% of the total weight of the composition, preferably from 0.5 to 15%. Preferred fillers are, for example, talc, zinc stearate, mica, kaolin, nylon powders (in particular Orgasol), polyethylene powders, Teflon, starch, boron nitride, microspheres of copolymers, such as Expancel (Nobel Industrie), Polytrap (Dow Corning) and silicone resin microbeads (Tospearl from Toshiba, for example).

The composition of the invention can advantageously comprise a solid or pasty fatty phase comprising one or more gums and/or one or more waxes. The waxes can be hydrocarbon-comprising, fluorinated, and/or silicone waxes and can be vegetable, mineral, animal, and/or synthetic in origin. The waxes in particular exhibit a melting temperature of greater than 25° C. and preferably greater than 45° C.

Preferred waxes which can be used in the composition of the invention, are, for example, beeswax, carnauba or candelilla wax, paraffin wax, microcrystalline waxes, ceresin or ozokerite; synthetic waxes, such as polyethylene or Fischer-Tropsch waxes, and silicone waxes, such as alkyl or alkoxy dimethicones having from 16 to 45 carbon atoms.

The gums are generally high molecular weight PDMS gums and the pasty substances are generally hydrocarbon-comprising compounds, such as lanolins and derivatives thereof, or PDMS compounds.

The nature and the amount of the solid substances depend on the mechanical and textural properties desired. The waxes may be present in an amount ranging from 0 to 50% by weight of waxes with respect to the total weight of the composition and preferably from 5 to 30%.

The composition according to the invention can also comprise one or more cosmetically acceptable (acceptable tolerance, toxicology and feel) organic solvents. These organic solvents can represent from 0% to 98% of the total weight of the composition and can be chosen from hydrophilic organic solvents, lipophilic organic solvents, amphiphilic solvents and mixtures thereof.

Preferred hydrophilic organic solvents are, for example, linear or branched lower monoalcohols having from 1 to 8 carbon atoms, polyols, mono- or dialkylisosorbide, the alkyl groups of which have from 1 to 5 carbon atoms, glycol ethers or fatty esters.

The composition may be in the form of a powder, a cream, an ointment, a fluid lotion, a supple paste with a dynamic viscosity ranging from 1 to 40 Pa.s, measured at 25° C. with a Contraves TV rotary viscometer having a Ms-r3 or Ms-r4 rotating element at a frequency of 60 Hz, or a salve, a cast or a moulded solid, in particular as a stick or in a dish.

The composition according to the invention may advantageously be used for making up the skin, and/or lips and/or superficial body growths, depending on the nature of the constituents used. In particular, the composition of the invention may be a tube of lipstick or a lip gloss which can be used by itself or to apply to a lipstick film, in particular in order to increase its gloss and/or colour (top coat). It may also constitute a solid foundation, a product for concealing rings under the eyes, an eyeliner, mascara, an eyeshadow, a powder or a blusher. These compositions can, in addition, comprise cosmetic or dermatological active principles for the purpose in particular of introducing a care or treating aspect into the composition. Thus, the composition may additionally comprise vitamins and other lipophilic active principles (lanolin or UVA screening agent) or hydrophilic active principles (moisturizers, such as glycerol).

Another aspect of the invention is a cosmetic use of the above composition for caring for, and/or making up, and/or protecting the skin, and/or lips and/or keratinous fibres and a use of this composition for the preparation of a salve intended to treat and/or protect the skin and/or lips. Yet another aspect of the invention is a process for the cosmetic treatment of the skin, and/or lips and/or keratinous fibres, which comprises applying the composition defined above to the skin, and/or lips and/or keratinous fibres.

More specifically, one aspect of the invention is a lip product or a blusher.

The composition of the invention may be obtained by heating the various constituents to the melting temperature of the highest-melting waxes and then casting the molten mixture in a mould (dish or thimble). It can also be obtained by extrusion, as disclosed in Application EP-A-667,146, the disclosure of which is specifically incorporated by reference herein.

Another aspect of the invention is the use, in a coloured cosmetic composition, of a colouring agent as described above in order to protect the skin, and/or lips and/or keratinous fibres against the damaging effects of free radicals and/or to combat cutaneous signs of ageing, in particular photoinduced ageing. These signs of ageing are in particular wrinkles, fine lines or flaccid and/or yellowed skin.

Yet another aspect of the invention is a process for the cosmetic protection of the skin, and/or lips and/or keratinous fibres against the damaging effects of free radicals and/or for combating cutaneous signs of photoinduced ageing, which comprises applying the composition as defined above to the skin, and/or lips and/or keratinous fibres.

The composition examples below are given by way of illustration and without a limiting nature.

EXAMPLE 1

Lipstick:

| Polyethylene wax | 14 g |
|---|---|
| Sesame oil | 78 g |
| DPP pigment (Formula B) | 5 g |
| Titanium dioxide | 3 g |

Procedure:

Homogenization of the oil and pigment mixture for 45 minutes in an oil bath, passing the mixture 3 times in succession through a triple roll mill, homogenization of the oil and pigment mixture for 30 minutes in an oil bath, moulding in a mould at 42° C. and 30 minutes in a freezer.

A lipstick is obtained which has an intense vermillion colour, has high coverage, is glossy, is stable to light and leaves no mark after it has been removed.

EXAMPLE 2

Blusher:

| Talc | 38 g |
|---|---|
| Mica | 20 g |
| Bismuth oxychloride | 8 g |
| Zinc stearate | 3 g |
| Nylon powder | 20 g |
| DPP pigment (Formula B) | 5 g |
| Fatty binder (*) | q.s. for 100 g |

(*) Mixture of Carbon-Comprising Oils Containing:
3.6 g of capric/caprylic acid triglycerides,
2.0 g of hydrogenated isoparaffin (non-volatile),
1.0 g of jojoba oil.

Procedure:

Premixing of all the fillers and pigments, 5 minutes with a Lödige device (powder mixer/homogenizer), Addition of the organic binder, 5 minutes with a Lödige device, Air jet milling (Chrispro), Sieving at 160 microns.

EXAMPLE 3

Lip Lacquer

Aqueous dispersion of acrylic/styrene polymer

| (Neocryl A-1052 of Zeneca) | 20% active matter |
|---|---|
| Acetyltributylcitrate | 2.5% |
| DPP pigment | 1.5% |
| Rouge Flaming (CI 12085) | 1.5% |
| glycerin | 1.25% |
| water | q.s. 100% |

What is claimed is:

1. A coloured composition for topical application comprising a pigment of formula (A):

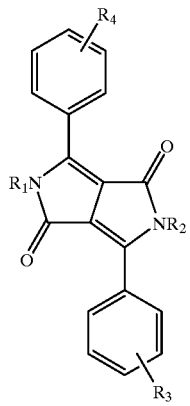

in which $R_1$ and $R_2$ independently represent a hydrogen atom, a $C_1$ to $C_{18}$ alkyl radical, a $C_3$ to $C_{12}$ alkenyl radical, a $C_2$ to $C_5$ alkoxycarbonyl radical or a phenyl radical which is optionally substituted by a halogen, and $R_3$ and $R_4$ independently represent a hydrogen atom, a $C_1$ to $C_{18}$ alkyl radical, a $C_1$ to $C_4$ alkoxy radical, a halo radical or a phenyl radical, or a —SO₃M group with M being a hydrogen atom, a metal atom or an ammonium group, it being possible for the alkyl, alkenyl and alkoxy radicals to be linear or branched.

2. The composition according to claim 1, wherein $R_1$ and $R_2$ independently represent a hydrogen atom or a methyl or 4-chlorophenyl radical.

3. The composition according to claim 1 wherein $R_3$ and $R_4$ independently represent a hydrogen atom, a 4-chloro radical or a 4-tert-butyl radical.

4. The composition according to claim 1, wherein said pigment is pyrrolo[3,4-c]pyrrole-1,4-dione of formula (B):

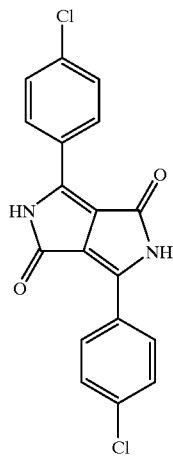

5. The composition according to claim 1, wherein said pigment is chosen from

Cromophtal DPP Red BP P—CI Pigment Red 254-No. CI 56110;

Cromophtal DPP Red BP—CI Pigment Red 254-No. CI 56110;

Irgazine DPP Red 5G—CI Pigment Red 255;

Irgazine DPP Rubine TR—CI Pigment Red 264;

Irgazine DPP Red 5049 B—CI Pigment Red 270; and

Irgazine Orange RA—CI Pigment Orange 73.

6. The composition according to claim 1, wherein said pigment is present in an amount ranging from 0.01 to 50% by weight with respect to the weight of the composition.

7. The composition according to claim 6, wherein said pigment is present in an amount ranging from 1 to 25% by weight with respect to the weight of the composition.

8. A product for making up human skin, lips and/or keratinous fibres comprising said pigment of formula (A):

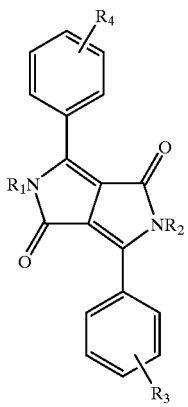

in which $R_1$ and $R_2$ independently represent a hydrogen atom, a $C_1$ to $C_{18}$ alkyl radical, a $C_3$ to $C_{12}$ alkenyl radical, a $C_2$ to $C_5$ alkoxycarbonyl radical or a phenyl radical which is optionally substituted by a halogen, and $R_3$ and $R_4$ independently represent a hydrogen atom, a $C_1$ to $C_{18}$ alkyl radical, a $C_1$ to $C_4$ alkoxy radical, a halo radical or a phenyl radical, or a —SO₃M group with M being a hydrogen atom, a metal atom or an ammonium group, it being possible for the alkyl, alkenyl and alkoxy radicals to be linear or branched.

9. The product according to claim 8, wherein said product is a nail varnish, a mascara, an eyeliner, a hair composition of lacquer type, a lipstick, a lip gloss, a foundation, a product for concealing rings under the eyes, a face powder, an eyeshadow, a powder, a blusher or a body make-up.

10. The composition according to claim 1, wherein said composition further comprises a medium in the form of a suspension, a dispersion or solution in organic solvent or aqueous/alcoholic medium, optionally thickened or gelled; an oil-in-water, water-in-oil or multiple emulsion; a gel or foam; an emulsified gel; a dispersion of vesicles; a two-phase or multiple-phase lotion; a spray; a loose, compacted or cast powder; or an anhydrous paste.

11. The composition according to claim 10, wherein said vesicles are selected from ionic and non-ionic lipids.

12. The composition according to claim 10, wherein said composition may additionally comprise a surfactant, a film forming polymer, or a fatty phase.

13. The composition according to claim 12, where said surfactant is present in an amount ranging from 0.01 to 30% by weight with respect to the total weight of the composition.

14. The composition according to claim 12, wherein said film-forming polymer is chosen from nitrocellulose, hydrocarbons-comprising resins and silicone resins.

15. The composition according to claim 1, further comprising a fatty phase, wherein said fatty phase is chosen from oils, waxes, gums, and pasty fatty substances.

16. The composition according to claim 15, wherein said oils are chosen from hydrocarbon-comprising oils of animal origin; vegetable hydrocarbon-comprising oils; linear and branched hydrocarbons of mineral and synthetic origin; synthetic esters and ethers; hydroxylated esters; polyol esters; fatty alcohols; partially hydrocarbon-comprising or silicone-comprising fluorinated oils; silicone oils; and mixtures thereof.

17. The composition according to claim 16, wherein said vegetable hydrocarbon-comprising oils are chosen from liquid triglycerides of fatty acids comprising 4 to 10 carbon atoms; heptanoic and octanoic acids; sunflower, maize, soybean, grapeseed, sesame, apricot, macadamia, castor and avocado oils; triglycerides of caprylic/capric acids; jojoba oil; and karite butter.

18. The composition according to claim 16, wherein said linear and branched hydrocarbons are chosen from liquid paraffins and derivatives thereof, petroleum jelly, polydecenes and hydrogenated polyisobutene.

19. The composition according to claim 16, wherein said synthetic esters and ethers are chosen from esters and ethers of fatty acids, purcellin oil, isopropyl myristate, 2-ethylhexyl palmitate, 2-octyldodecyl stearate, 2-octyidodecyl erucate and isostearyl isostearate.

20. The composition according to claim 16, wherein said hydroxylated esters are chosen from isostearyl lactate, octyl hydroxystearate, octyidodecyl hydroxystearate, diisostearyl maleate, triisocetyl citrate, and heptanoates, octanoates and decanoates of fatty alcohols.

21. The composition according to claim 16, wherein said polyol esters are chosen from propylene glycol dioctanoate, neopentyl glycol diheptanoate, diethylene glycol diisononanoate and pentaerythritol esters.

22. The composition according to claim 16, wherein said fatty alcohols are chosen from fatty alcohols having from 12 to 26 carbon atoms.

23. The composition according to claim 22, wherein said fatty alcohols are selected from octyldodecanol, 2-butyloctanol, 2-hexyldecanol, 2-undecylpentadecanol and oleyl alcohol.

24. The composition according to claim 16, wherein said silicone oils are chosen from linear and cyclic, volatile and non volatile polydimethylsiloxanes.

25. The composition according to claim 24, wherein said polydimethylsiloxanes are selected from cyclomethicones and dimethicones, optionally comprising a phenyl group.

26. The composition according to claim 24, wherein said polydimethylsiloxanes are selected from phenyl trimethicones, phenyltrimethylsiloxydiphenylsiloxanes, diphenylmethyldimethyltrisiloxanes, diphenyl dimethicones, phenyl dimethicones and polymethylphenyl-siloxanes.

27. The composition according to claim 15, wherein said oils are presents in an amount ranging from 0 to 100% by weight with respect to the total weight of the fatty phase.

28. The composition according to claim 15, wherein said waxes are chosen from beeswax, carnauba wax, candelilla wax, paraffin wax, microcrystalline waxes, ceresin, ozokerite; synthetic waxes and silicone waxes.

29. The composition according to claim 28, wherein said synthetic waxes are chosend from polyethylene and Fischer-Tropsch waxes, and wherein said silicone waxes are selected from alkyl and alkoxy dimethicones having from 16 to 45 carbon atoms.

30. The composition according to claim 15, wherein said waxes are present in an amount ranging from 0 to 50% by weight of waxes with respect to the total weight of the composition.

31. The composition according to claim 30, wherein said waxes are present in an amount ranging from 5 to 30%.

32. The composition according to claim 15, wherein said gums and pasty substances are chosen from hydrocarbon-comprising compounds and polydimethylsiloxane compounds.

33. The composition according to claim 16 wherein said hydrocarbon-comprising compounds are selected from lanolins and derivatives thereof.

34. The composition according to claim 1, further comprising an additional particulate phase present in an amount ranging up to 35% of the total weight of the composition.

35. The composition according to claim 1, wherein said composition is in an anhydrous form.

36. A method for caring for, making up, or protecting the skin, lips, or keratinous fibres comprising applying to said skin, lips, or keratinous fibres an effective amount of a composition comprising a pigment of formula (A):

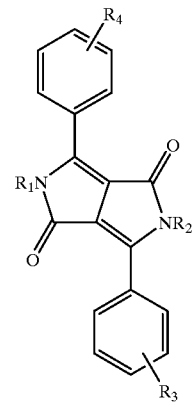

in which $R_1$ and $R_2$ independently represent a hydrogen atom, a $C_1$ to $C_{18}$ alkyl radical, a $C_3$ to $C_{12}$ alkenyl radical, a $C_2$ to $C_5$ alkoxycarbonyl radical or a phenyl radical which is optionally substituted by a halogen, and $R_3$ and $R_4$ independently represent a hydrogen atom, a $C_1$ to $C_{18}$ alkyl radical, a $C_1$ to $C_4$ alkoxy radical, a halo radical or a phenyl radical, or a —$SO_3M$ group with M being a hydrogen atom, a metal atom or an ammonium group, it being possible for the alkyl, alkenyl and alkoxy radicals to be linear or branched.

37. A method for treating or protecting the skin or lips comprising applying to said skin or lips an effective amount a salve comprising a composition comprising a pigment of formula (A):

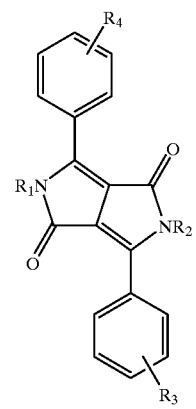

in which $R_1$ and $R_2$ independently represent a hydrogen atom, a $C_1$ to $C_{18}$ alkyl radical, a $C_3$ to $C_{12}$ alkenyl radical, a $C_2$ to $C_5$ alkoxycarbonyl radical or a phenyl radical which is optionally substituted by a halogen, and $R_3$ and $R_4$ independently represent a hydrogen atom, a $C_1$ to $C_{18}$ alkyl radical, a $C_1$ to $C_4$ alkoxy radical, a halo radical or a phenyl radical, or a —$SO_3M$ group with M being a hydrogen atom, a metal atom or an ammonium group, it being possible for the alkyl, alkenyl and alkoxy radicals to be linear or branched.

38. A method of protecting the skin, lips, or keratinous fibres against the damaging effects of free radicals or combating cutaneous signs of ageing comprising applying to said skin, lips, or keratinous fibres an effective amount of a composition comprising a pigment of formula (A):

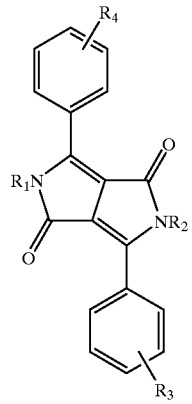

in which $R_1$ and $R_2$ independently represent a hydrogen atom, a $C_1$ to $C_{18}$ alkyl radical, a $C_3$ to $C_{12}$ alkenyl radical, a $C_2$ to $C_5$ alkoxycarbonyl radical or a phenyl radical which is optionally substituted by a halogen, and $R_3$ and $R_4$ independently represent a hydrogen atom, a $C_1$ to $C_{18}$ alkyl radical, a $C_1$ to $C_4$ alkoxy radical, a halo radical or a phenyl radical, or a —$SO_3M$ group with M being a hydrogen atom, a metal atom or an ammonium group, it being possible for the alkyl, alkenyl and alkoxy radicals to be linear or branched.

39. A method of protecting skin, lips or keratinous fibres against the damaging effects of free radicals or combating cutaneous signs of ageing comprising the step of including an effective amount of a composition comprising a pigment of formula (A):

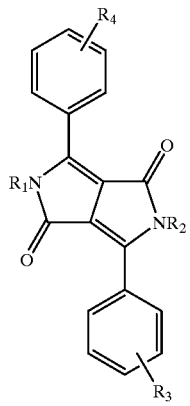

in which $R_1$ and $R_2$ independently represent a hydrogen atom, a $C_1$ to $C_{18}$ alkyl radical, a $C_3$ to $C_{12}$ alkenyl radical, a $C_2$ to $C_5$ alkoxycarbonyl radical or a phenyl radical which is optionally substituted by a halogen, and $R_3$ and $R_4$ independently represent a hydrogen atom, a $C_1$ to $C_{18}$ alkyl radical, a $C_1$ to $C_4$ alkoxy radical, a halo radical or a phenyl radical, or a —$SO_3M$ group with M being a hydrogen atom, a metal atom or an ammonium group, it being possible for the alkyl, alkenyl and alkoxy radicals to be linear or branched, in a cosmetic composition for the purpose of protecting said skin, lips, or keratinous fibres against the damaging effects of free radicals or combating cutaneous signs of ageing.

* * * * *

UNITED STATES PATENT AND TRADEMARK OFFICE
CERTIFICATE OF CORRECTION

PATENT NO. : 6,042,842
DATED : March 28, 2000
INVENTOR(S) : Patricia LEMANN, et al.

It is certified that error appears in the above-indentified patent and that said Letters Patent is hereby corrected as shown below:

In claim 19, column 11, line 15, "2-octyidodecyl" should read --2-octyldodecyl--.

In claim 27, column 11, line 44, "presents" should read --present--.

In claim 37, column 12, line 39, "a salve" should read --of a salve--.

Signed and Sealed this

Twentieth Day of March, 2001

Attest:

NICHOLAS P. GODICI

Attesting Officer

Acting Director of the United States Patent and Trademark Office